(12) United States Patent
Rolfe et al.

(10) Patent No.: US 8,801,674 B2
(45) Date of Patent: Aug. 12, 2014

(54) AUTOINJECTORS

(75) Inventors: Steven Mark Guy Rolfe, Oxfordshire (GB); Max Roland Allen, Oxfordshire (GB); Jeremy Marshall, Oxford (GB)

(73) Assignee: Owen Mumford Limited, Oxford (GB)

( * ) Notice: Subject to any disclaimer, the term of this patent is extended or adjusted under 35 U.S.C. 154(b) by 194 days.

(21) Appl. No.: 13/142,717

(22) PCT Filed: Dec. 21, 2009

(86) PCT No.: PCT/GB2009/051750
§ 371 (c)(1),
(2), (4) Date: Sep. 8, 2011

(87) PCT Pub. No.: WO2010/076569
PCT Pub. Date: Jul. 8, 2010

(65) Prior Publication Data
US 2011/0313364 A1 Dec. 22, 2011

Related U.S. Application Data

(60) Provisional application No. 61/143,230, filed on Jan. 8, 2009.

(30) Foreign Application Priority Data
Dec. 31, 2008 (GB) .................................. 0823693.7

(51) Int. Cl.
*A61M 5/31* (2006.01)
*A61M 5/32* (2006.01)
*A61M 5/315* (2006.01)
*A61M 5/24* (2006.01)
*A61M 5/20* (2006.01)

(52) U.S. Cl.
CPC ......... *A61M 5/24* (2013.01); *A61M 2005/2488* (2013.01); *A61M 2005/2407* (2013.01); *A61M 2005/206* (2013.01); *A61M 5/2033* (2013.01); *A61M 2005/3247* (2013.01); *A61M 5/326* (2013.01)
USPC ............................ 604/198; 604/218; 604/242

(58) Field of Classification Search
USPC ......................................... 604/198, 218, 242
See application file for complete search history.

(56) References Cited

U.S. PATENT DOCUMENTS 3,055,362 A 9/1962 Uytenbogaart
5,263,934 A * 11/1993 Haak .............................. 604/110

(Continued)

FOREIGN PATENT DOCUMENTS

EP 1 285 674 A1 2/2003
GB 2 437 922 A 11/2007

(Continued)

OTHER PUBLICATIONS

International Search Report, dated Jul. 1, 2010, from corresponding PCT application.

(Continued)

*Primary Examiner* — Emily Schmidt
*Assistant Examiner* — Lauren M Peng
(74) *Attorney, Agent, or Firm* — Young & Thompson

(57) ABSTRACT

An autoinjector includes front and rear separable housing parts 10, 12. These are connected by a rotary coupling action such as by bayonet coupling and the relative rotation action turns a needle shield 20 from a locked position in which it is both locked against longitudinal movement and acts as a shutter obscuring the contents of the syringe to an open position where the contents of the syringe are visible and the shield portion is freed for longitudinal movement. Connecting and securing the rear portion 12 on the front portion 11 therefore unlocks the needle shield 20 for operation. On completion of an injection, uncoupling of the front and rear portions returns the needle shield 20 to its locked position so the front portion may be disposed of safely.

19 Claims, 10 Drawing Sheets

(56) References Cited

U.S. PATENT DOCUMENTS

| | | |
|---|---|---|
| 6,203,530 B1 | 3/2001 | Stewart, Sr. |
| 6,752,782 B2 * | 6/2004 | Liao .............................. 604/110 |
| 6,830,560 B1 | 12/2004 | Gross et al. |
| 7,033,343 B2 * | 4/2006 | McWethy et al. ............. 604/506 |
| 7,794,432 B2 | 9/2010 | Young et al. |
| 8,177,745 B2 | 5/2012 | Brechbuehler et al. |
| 2003/0229314 A1 | 12/2003 | McWethy et al. |
| 2005/0273061 A1 | 12/2005 | Hommann et al. |
| 2006/0030819 A1 | 2/2006 | Young et al. |
| 2006/0153693 A1 | 7/2006 | Fiechter et al. |
| 2006/0270985 A1 | 11/2006 | Hommann et al. |
| 2008/0071225 A1 * | 3/2008 | Hommann et al. ........... 604/198 |
| 2008/0228143 A1 | 9/2008 | Stamp |

FOREIGN PATENT DOCUMENTS

| | | |
|---|---|---|
| JP | H021289 A | 1/1990 |
| JP | 2001521792 A | 11/2001 |
| JP | 2006507060 A | 3/2006 |
| JP | 2006255272 A | 9/2006 |
| JP | 2008508950 A | 3/2008 |
| WO | 94/21316 A1 | 9/1994 |
| WO | 96/26754 A2 | 9/1996 |
| WO | 2004/047892 A1 | 6/2004 |
| WO | 2005/070481 A1 | 8/2005 |
| WO | 2008025179 A1 | 3/2008 |
| WO | 2009/022132 A2 | 2/2009 |

OTHER PUBLICATIONS

British Search Report, dated Sep. 17, 2009, from corresponding British application.

British Search Report, dated Apr. 30, 2009, from corresponding British application.

Translation of Japanese Office Action, dated Sep. 10, 2013, from corresponding JP application.

* cited by examiner

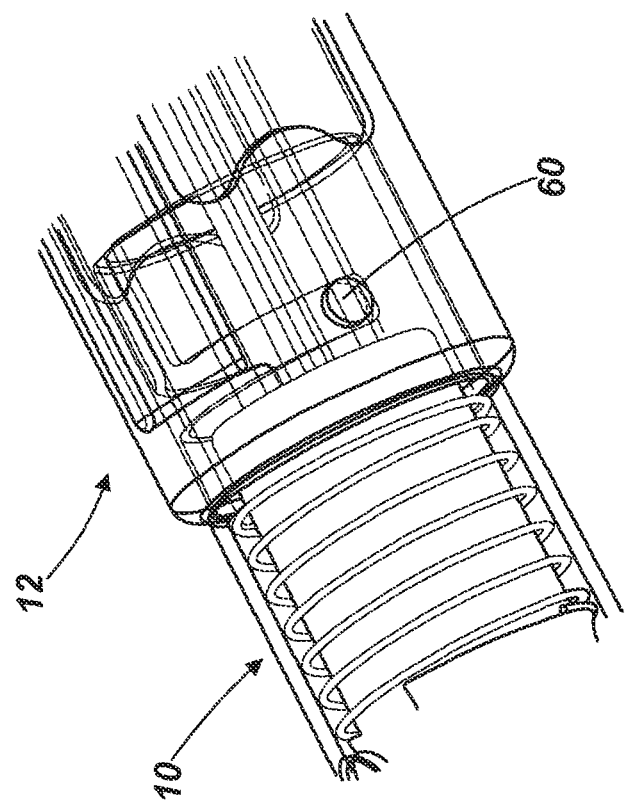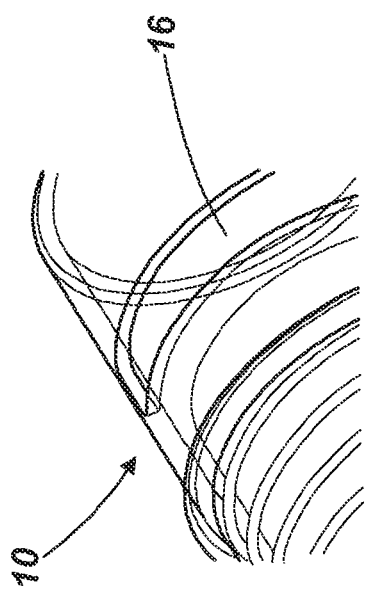
Fig. 10

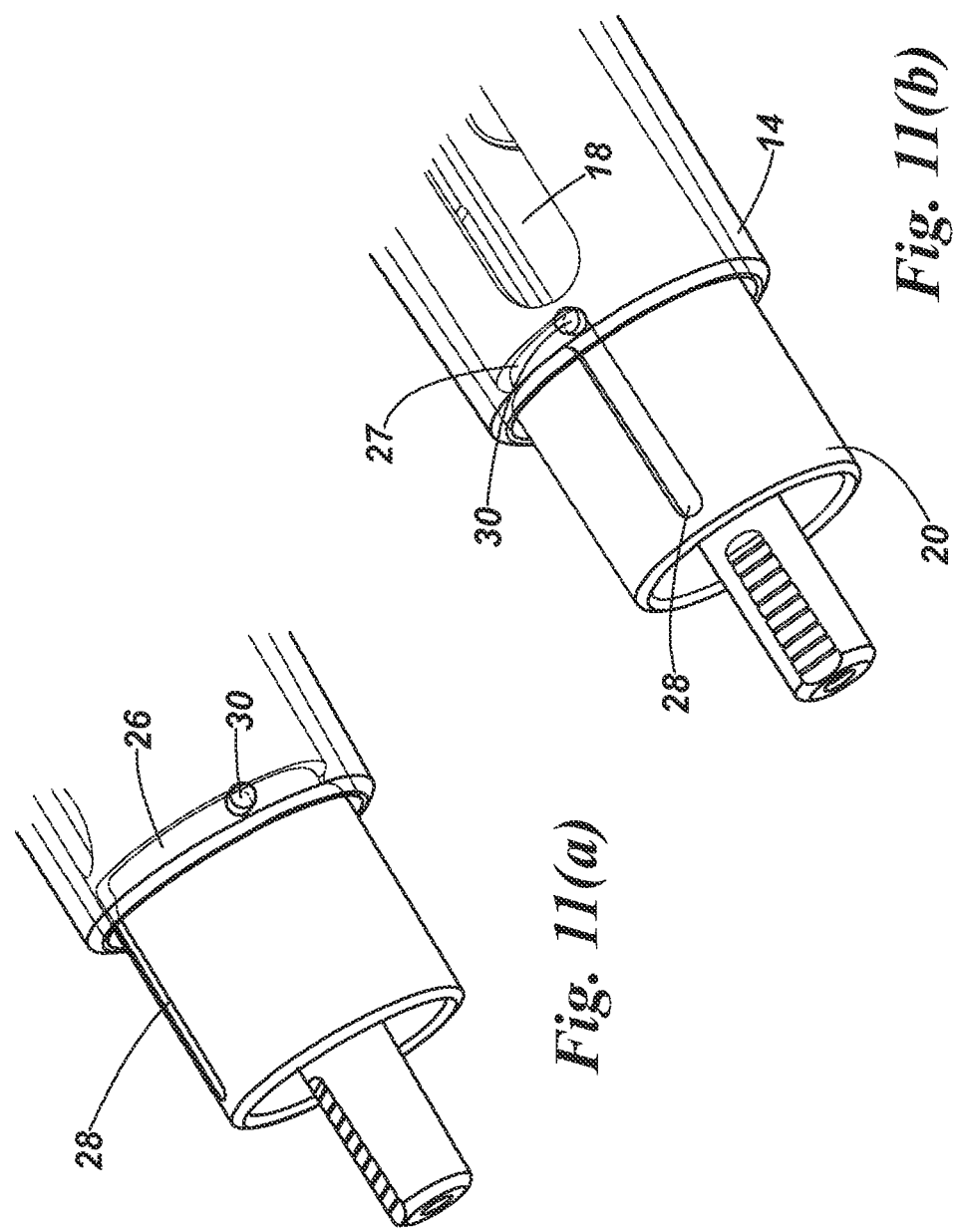

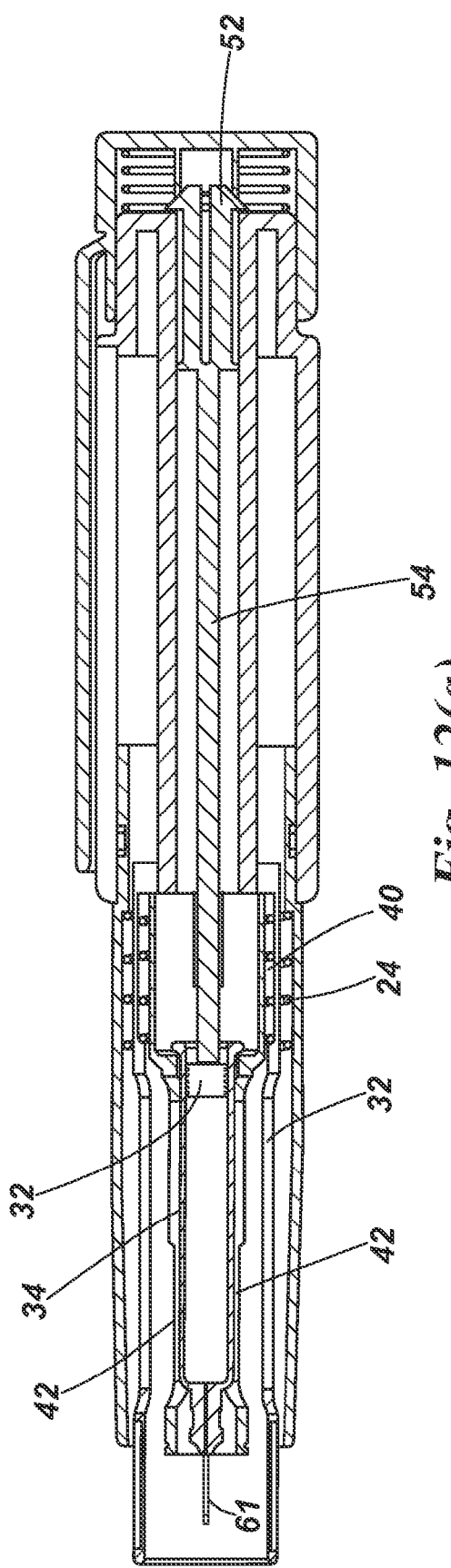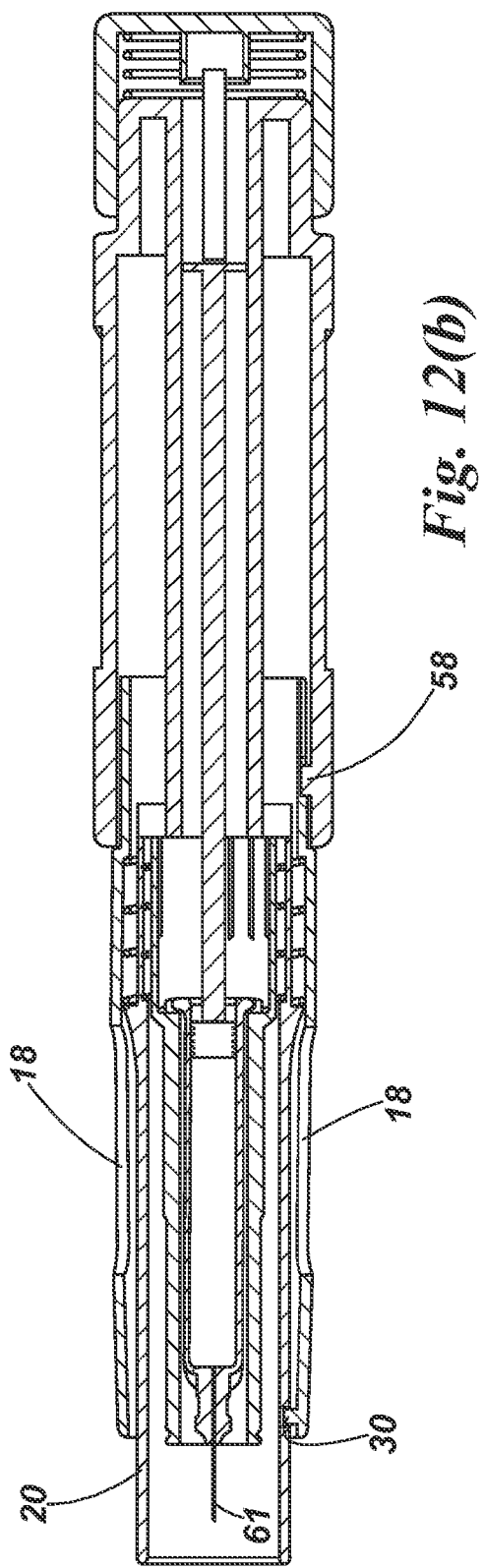

AUTOINJECTORS

This invention relates to autoinjectors and in particular, but not exclusively, to autoinjectors comprising front and rear separable housing parts that may be separated to allow insertion and withdrawal of a syringe.

In such devices there is a need to ensure that the device is left safe both before and after use, particularly when the front housing contains a syringe and has been separated from the rear housing.

Accordingly, in one aspect this invention provides an autoinjector comprising front and rear separable housing portions connectable and disconnectable by a coupling action, the rear housing portion containing a drive mechanism, the front housing portion being adapted in use to receive a syringe having a needle, the front housing portion including a generally cylindrical needle shield portion movable between an extended position in which it shields said syringe needle in use, and a retracted position in which the needle may be exposed, the autoinjector further including a locking arrangement which is effective to lock said shield against retraction movement and which is unlocked when said housing portions are connected and which is locked when said portions are disconnected.

In this arrangement therefore the needle shield is locked and unlocked automatically during or as a result of the coupling action and reversal thereof as the housing portions are connected and disconnected, to ensure that the shield is locked once the front housing has been separated.

The shield is preferably locked by a locking arrangement which comprises complementary locking surfaces disposed on the needle shield portion and the front housing portion respectively. Although we do not exclude the possibility of a linear locking arrangement, preferably the shield is locked by applying a relative angular movement. In a preferred arrangement the complementary surfaces include an internal projection on said front housing portion and a complementary groove on said shield portion, the groove having a rearward circumferential portion corresponding to the lock condition and, extending forwardly therefrom an axial portion allowing relative longitudinal movement of the needle shield. The inverse arrangement is also possible.

There are numerous ways in which the action of coupling the front and rear housings can effect unlocking of the needle shield portion. For example, where the front and rear housing portions are connected by a rotary coupling action (such as e.g. a bayonet coupling) the needle shield may have a rearward connection interface for being engaged by a complementary forward interconnection interface on the rear housing portion, whereby the action of coupling said front and rear housing portions causes said needle shield to rotate to unlock it. The forward and rearward connection interfaces may comprise longitudinally engageable non-circular male and female plug and socket portions.

The efficacy or shelf life of many medicaments may be degraded by prolonged exposure to light. Furthermore it is desirable for a user to be able to visually inspect the condition of a medicament in a syringe before making the injection, and also to check to see that the medicament has actually been dispensed. Accordingly, in a preferred embodiment, the autoinjector is designed so that, in use, the barrel of the syringe is visible through aligned apertures in two or more of the front housing portion, the needle shield, and a syringe carrier, when the shield is in the unlocked position, the apertures moving out of alignment when the shield is locked so the syringe is no longer visible, and the medicament is no longer exposed to light.

In another aspect, this invention provides an autoinjector comprising front and rear separable housing portions connectable and disconnectable by a coupling action, the rear housing portion combining a drive mechanism, the front housing portion being adapted in use to receive a syringe having a needle, and also having an inspection window through which the contents of the syringe may be viewed, the front housing portion including a shutter arrangement movable between an open position and a closed position, the shutter arrangement being opened when said housing portions are connected and being closed when said portions are disconnected.

Whilst the invention has been described above, it extends to any inventive combination of the features set out above or in the following description.

The invention may be performed in various ways, and an embodiment thereof will now be described by way of example only, reference being made to the accompanying drawings in which:

BRIEF DESCRIPTION OF THE DRAWINGS

FIG. 10 is a detailed view of the cooperating coupling parts;

FIGS. 11 (*a*) and (*b*) are detailed views of the locking arrangement between the needle shield and the casing in the locked and unlocked positions respectively;

FIGS. 12(*a*) and 12(*b*) are vertical and horizontal views through an autoinjector of this invention in the locked, primed condition, and FIGS. 13 (*a*), (*b*) and (*c*) show the autoinjector in its fired position with the needle shield still retracted; with the needle shield extended, and with the front and rear housing portions separated and the shield locked forward, respectively.

DETAILED DESCRIPTION OF THE PREFERRED EMBODIMENTS

Figure 1:
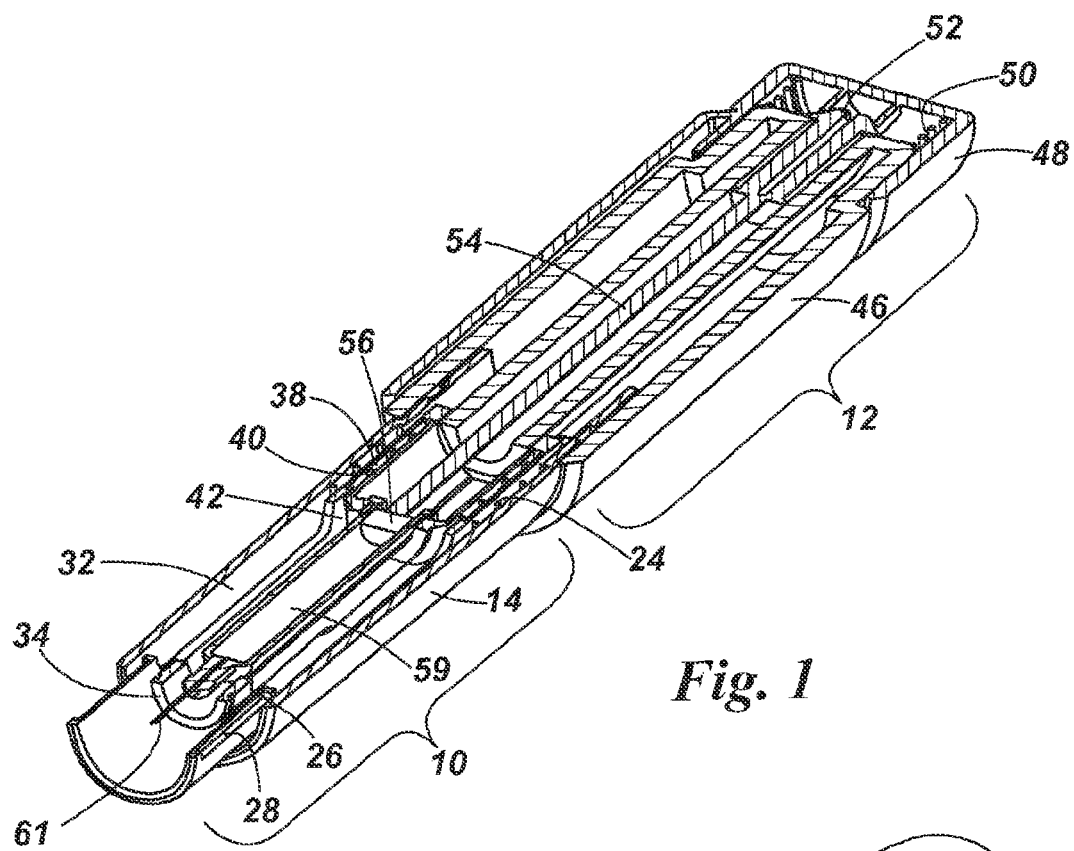
FIG. 1 is a horizontal section view through an autoinjector of this invention in the locked, primed position.
Figure 2:
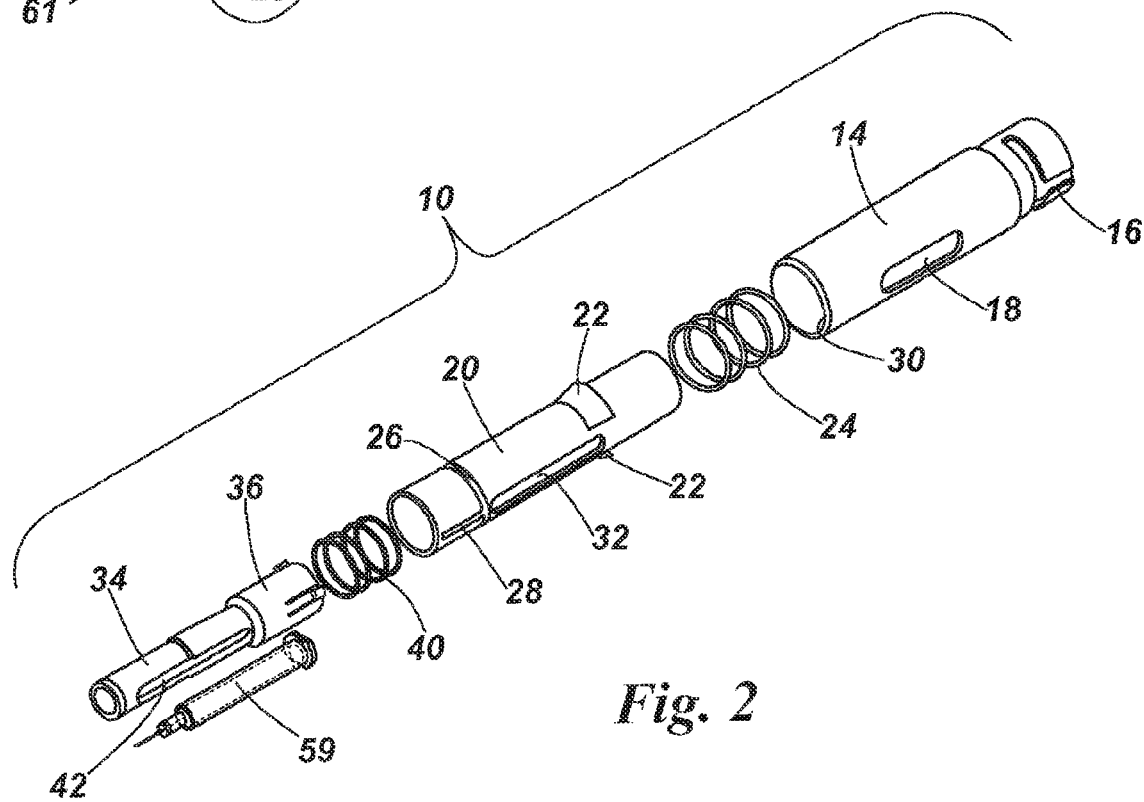
FIG. 2 is an exploded view of the components in the front housing.
Figure 3:
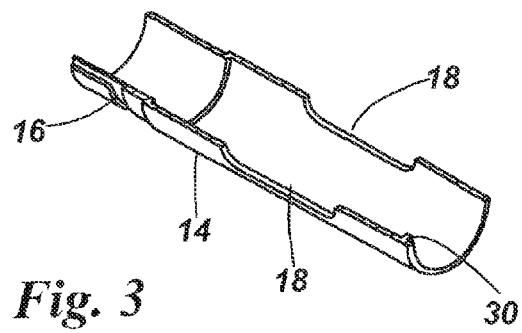
FIG. 3 is a horizontal section view on the lower half of the front casing looking from the front.

The autoinjector illustrated in the Figures comprises front and rear separable housing portions 10, 12 respectively. The portions 10, 12 are connected by a bayonet type coupling at their interface as to be described below. Referring to FIG. 2, the front housing portion 10 is made up of a front casing 14 with a T-shaped bayonet groove 16 at its rear end and twin elongate windows 18 in its side. Telescopically received within the front casing 14 is a needle shield 20 having raised spring seats 22 which cooperate with a compression spring 24 within the front casing to urge the needle shield forwards. The needle shield 20 has at its forward end a circumferential groove 26, the opposite ends of which lead to diametrically opposed axial grooves 28. The grooves cooperate with an internally projecting peg 30 (see FIG. 3) on the front inside of the front casing 14 to limit forward movement of the needle shroud 20. When the needle shield 20 and the front casing 14 are angularly disposed in a position in which the peg 30 is in the circumferential groove 26, the two are locked against axial movement. But when the peg 30 is in either axial groove 28, the needle shield can retract into the casing 14. The needle shroud 20 also has twin elongate windows 32 down its side.

Telescopically received within the needle shield 20 is a syringe carrier 34 having three sprung outwardly directed lugs 36 which run in an annular space 38 in the inner face of the needle shield 20 to limit relative movement of the syringe carrier 34 relative to the needle shield. The needle shield also has twin elongate windows 42 down its side. A compression spring 40 urges the syringe carrier 34 to a retracted position relative to the needle shield. The syringe carrier 34 and the needle shield 20 can move together rearwardly within the front casing 14 against the influence of the spring 24, when pressed against the injection site.

Figures 4, 5:
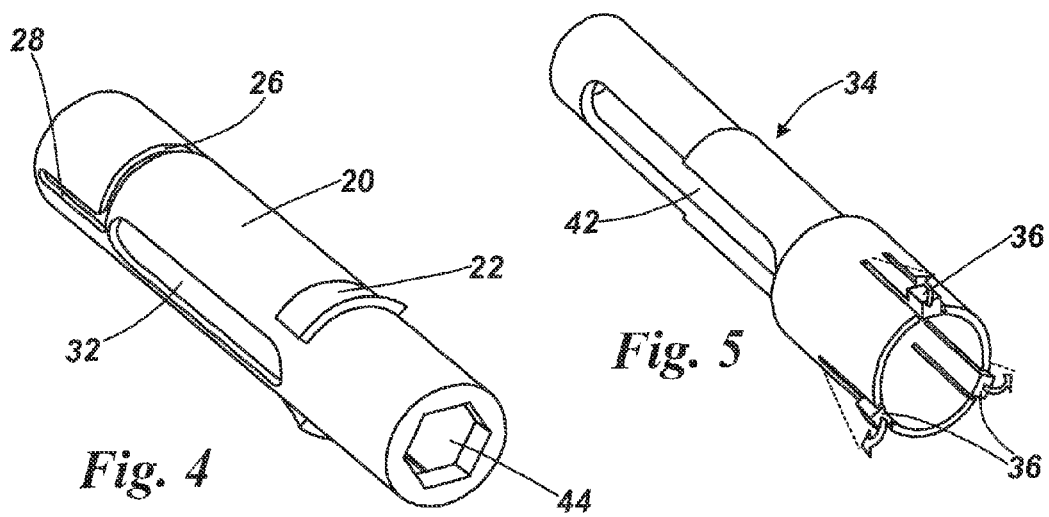
FIG. 4 is a perspective view of the needle shield looking from the rear.
FIG. 5 is a perspective view of the syringe housing looking from the rear.

As shown in FIG. 4, the rear end of the needle shield 20 is formed with a hexagonal drive socket 44.

Figures 6, 7:
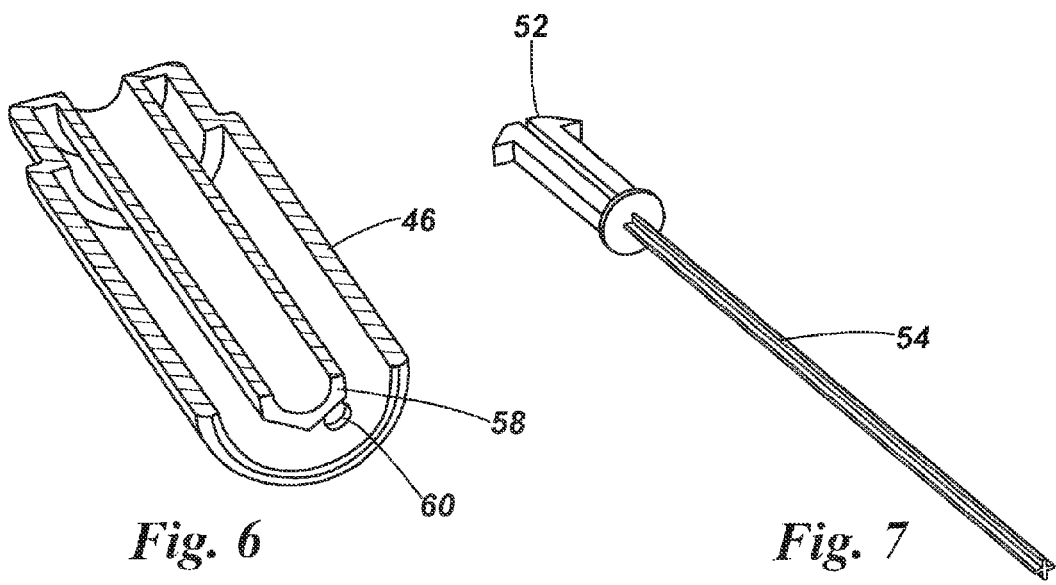
FIG. 6 is a horizontal section view on the firing body, looking rearwards.
FIG. 7 is a perspective view of the plunger.

The rear housing portion 12 comprises a firing body 46, having a firing button 48 sprung-loaded by a compression spring 50 on the rear end of the firing body 46. The firing button 48 can be pressed forwardly to release a split arrowhead latching arrangement 52 on the rear of a plunger 54 when the firing button is pushed, so that the plunger 54 can move forwardly under the influence of a main drive spring (not shown) to engage a bung 56 of a syringe indicated generally at 59. The firing body is illustrated in section in FIG. 6 and has a central hollow stem 58 of hexagonal outer form designed to be a driving fit with the hexagonal socket 44 on the needle shroud. The firing body also has a bayonet peg 60 which cooperates with the bayonet grooves 16 on the front casing 14.

The bayonet coupling is designed so that, when the front and rear housing portions are assembled together, the bayonet peg 60 has to be aligned with the axial part of the bayonet groove 16 thus angularly registering the front and rear portions before the hexagonal stem 58 enters the socket 44. This ensures that the two are always correctly aligned when the front and rear portions are assembled.

Figure 8:
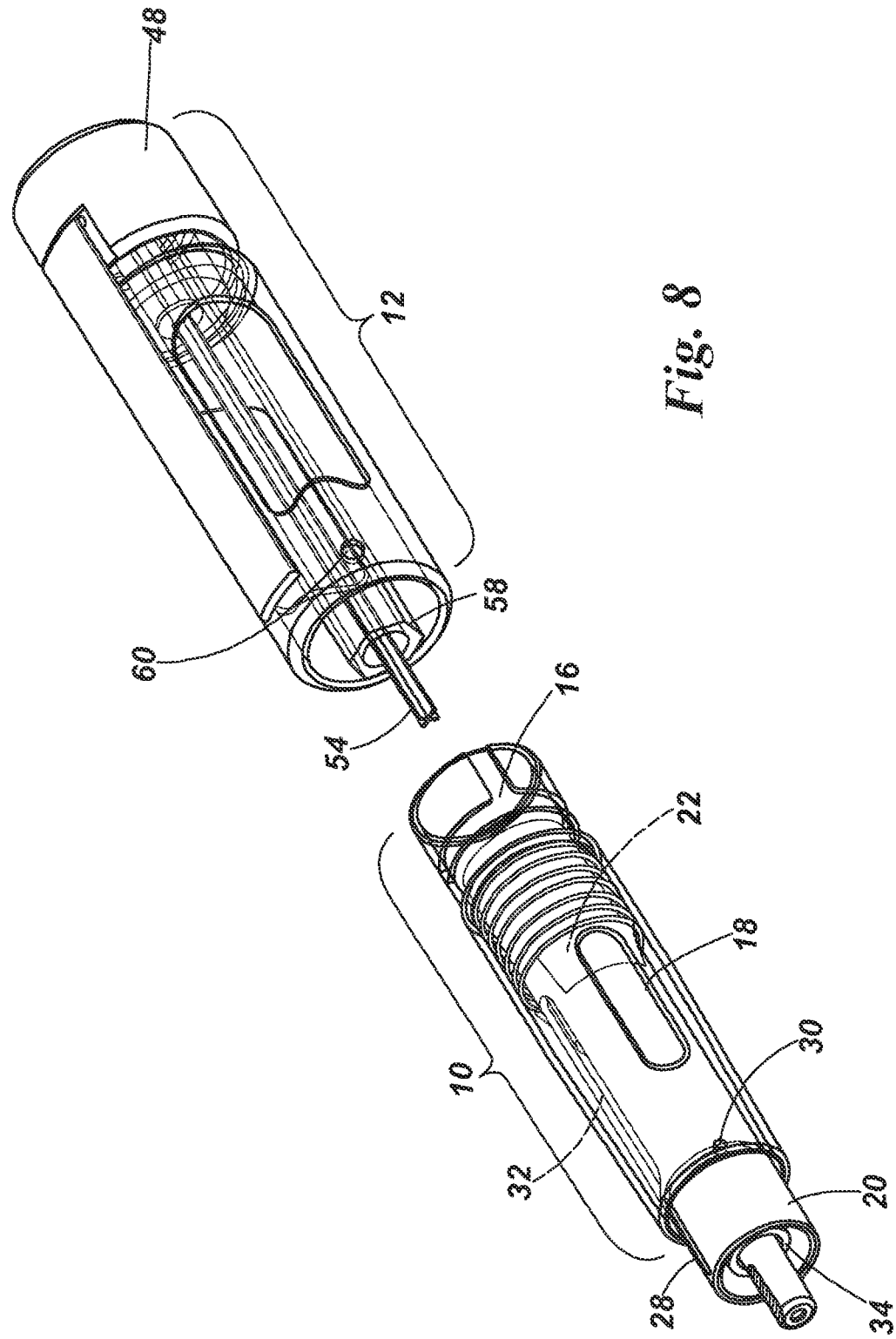
FIG. 8 is a perspective view of the front and rear housing portions prior to assembly.
Figure 9:
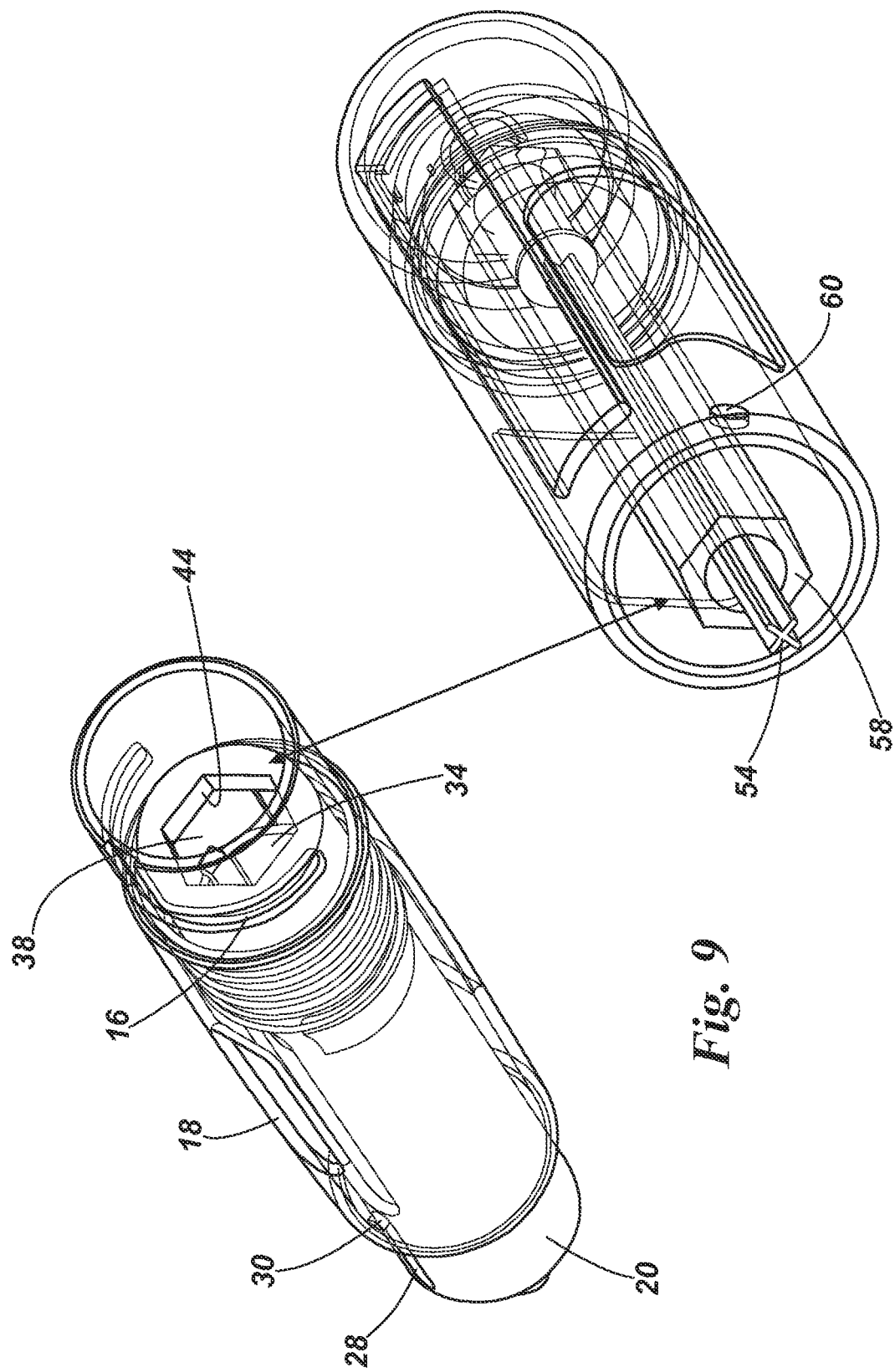
FIG. 9 shows the cooperating coupling parts of the front and rear housing portions.
Figure 13A:
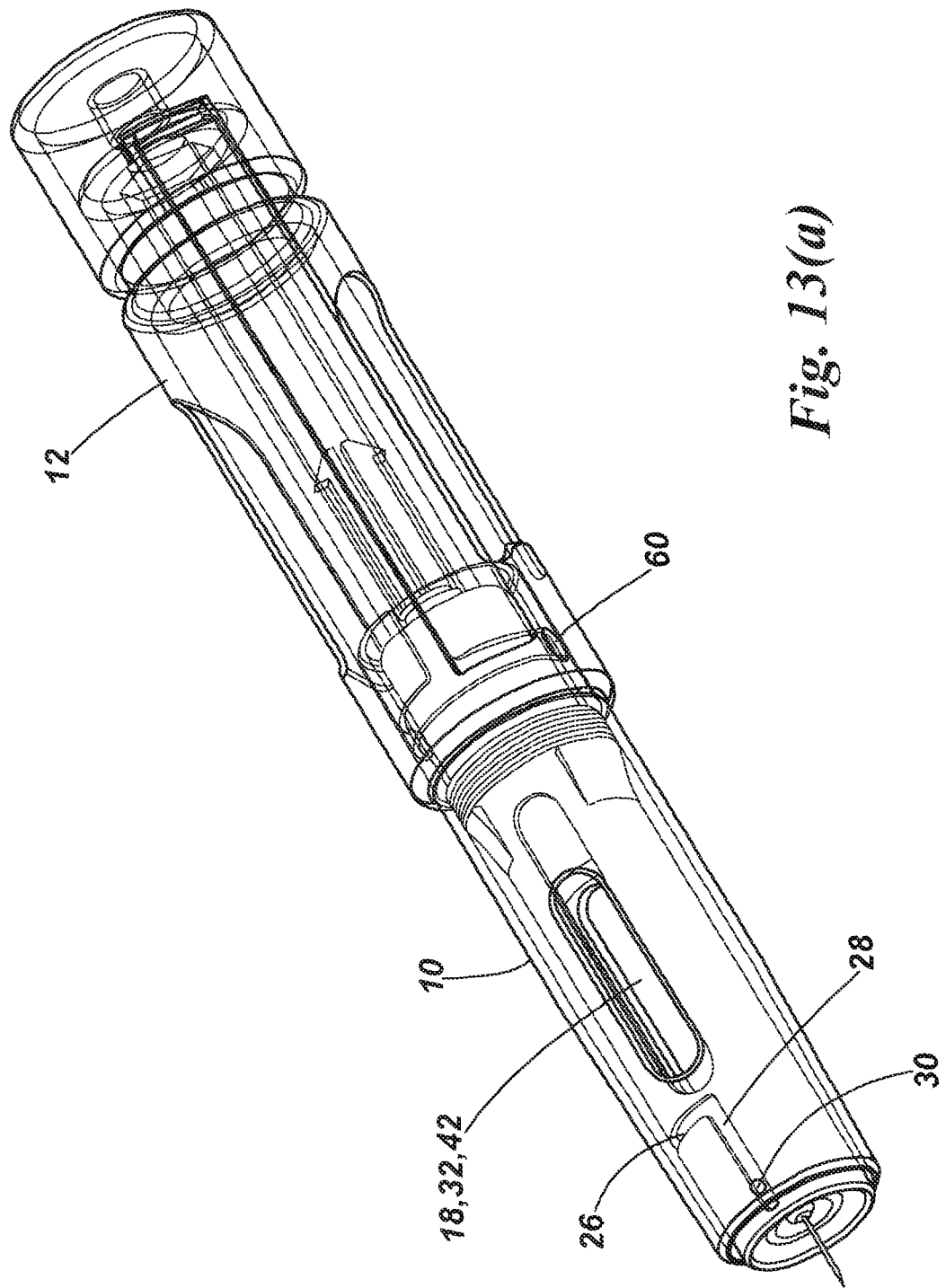

In operation of the device as seen in FIG. 8, the front and rear housing portions 10 and 12 are uncoupled and a syringe 59 is inserted into the syringe carrier 34. The rear housing portion 12 is offered up to the front housing portion 10 and the bayonet peg 60 enters the axial part of the bayonet groove 16. The two portions are then pushed together so that the peg 16 rides down the axial part of the bayonet groove 16. As this is done, the hexagonal stem 58 enters the hexagonal socket 44 as described above. The rear portion 12 is then twisted relative to the front portion to secure the bayonet coupling with the front housing portion, and this rotation is transmitted through the hexagonal stem 58 and the hexagonal socket 44 to the needle shroud 22. This causes the needle shroud to rotate so that the axial groove 28 becomes aligned with the peg 30 on the front casing as the bayonet peg 60 reaches its fully secured position at the end of the circumferential part of the bayonet groove 16. In this position the needle shroud is now capable of retraction movement, with the peg 30 passing along the axial groove 28. Also, in the unlocked position, the apertures 32 on the needle shroud 20 are now aligned with the aligned apertures 42 and 18 on the syringe carrier and the front casing 14 respectively as seen in the left hand parts of FIGS. 13(a) and (b), and so the syringe contents can be seen.

Figure 13B:
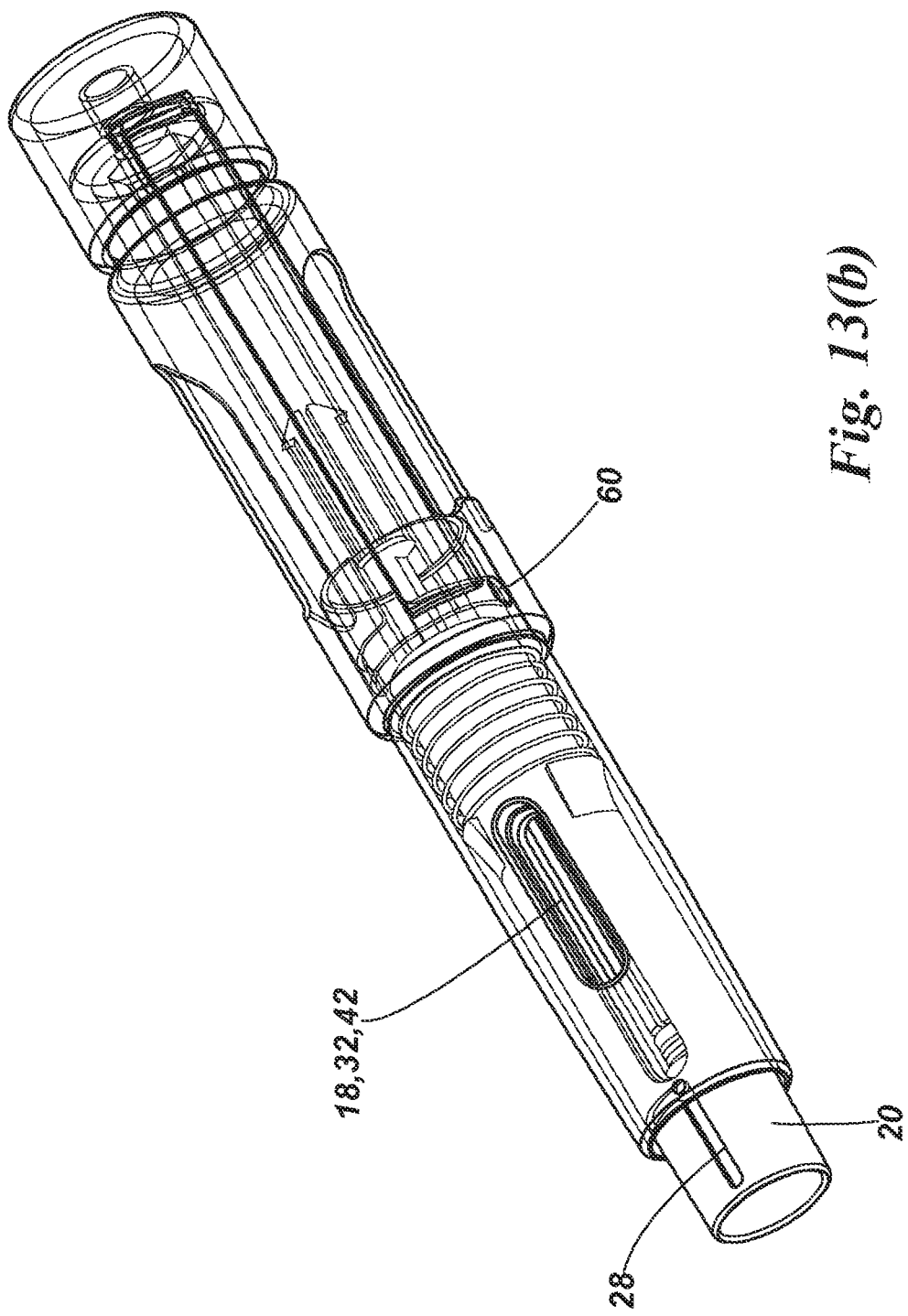

The device is offered up to the skin and pushed against the injection site so that the needle shield 20, and the syringe carrier 34 containing the syringe retracts into the casing. The device is then fired by pressing the firing button 48 which releases the plunger 54 to engage the bung initially to drive the syringe and the syringe carrier 34 forwards relative to the needle shield 20 against the bias of the spring 40 until the syringe carrier reaches its forwardmost position so that the needle 61 enters the flesh. Thereafter continued forward movement of the plunger drives the bung to expel a dose through the needle (FIG. 13(a)). After the injection is complete, the user may confirm this by visual inspection of the syringe through the aligned windows 18, 32 and 42. The device is then removed from the injection site and the springs 24 and 40 push the needle shield 20 to a forwardmost position, where the peg 30 is level with the circumferential groove 26 (FIG. 13(b)).

Figure 13C:
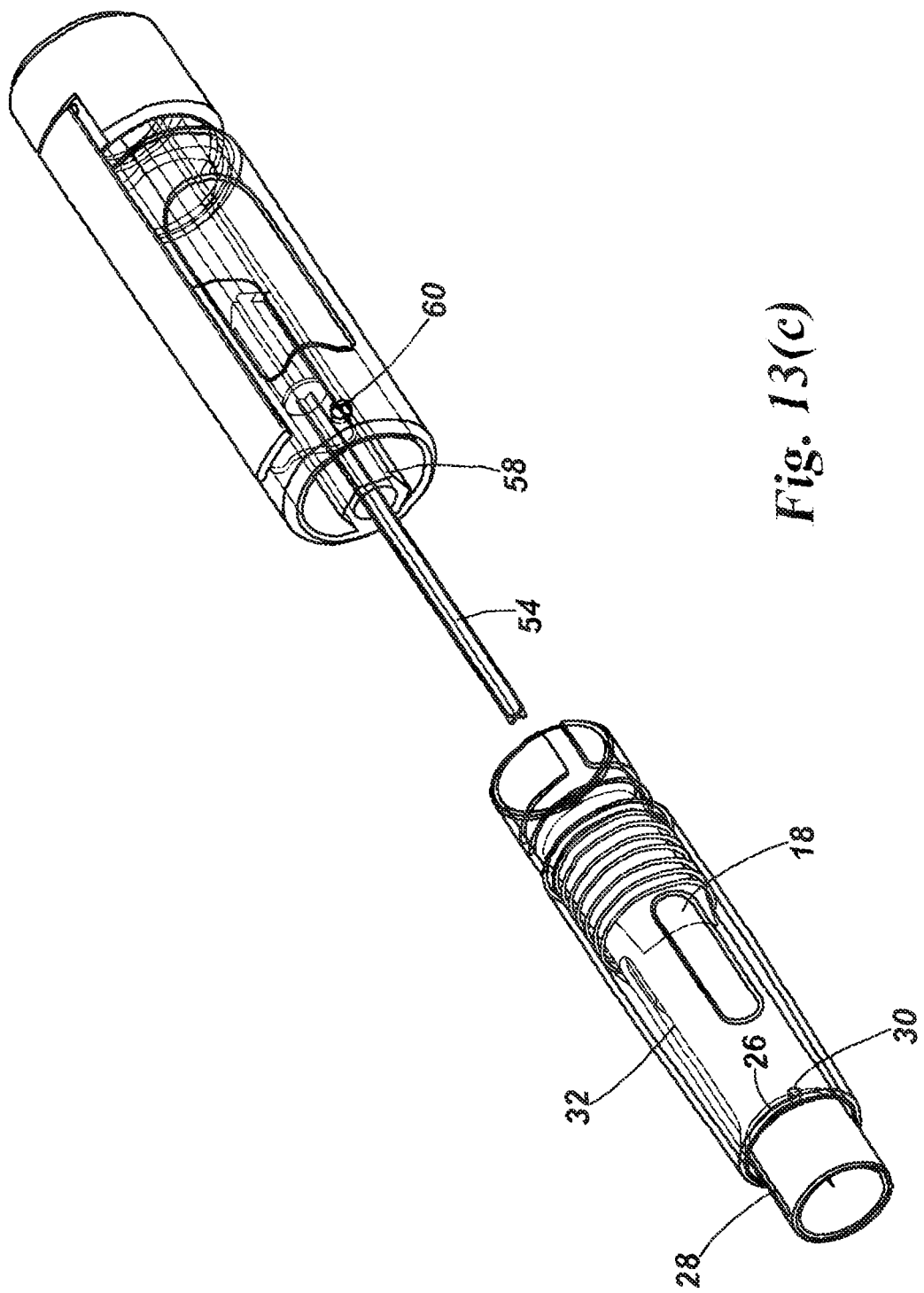

The device is then disassembled by undoing the bayonet coupling. As previously, rotation is transmitted from the hexagonal stem 58, and through the socket 44 to rotate the needle shield back to its original position. It then again acts as a shutter between the windows 18 and 42 and the peg 30 locates in the circumferential groove 26 thereby locking the shroud out against retraction movement (FIG. 13(c)). The front portion is therefore rendered safe for disposal.

The invention claimed is:

1. An autoinjector, comprising:
   front (10) and rear (12) separable housing portions connectable and disconnectable by a coupling action,
   the rear housing portion containing a drive mechanism (54), and
   the front housing portion being adapted in use to receive a syringe having a needle,
   the front housing portion including a needle shield portion movable between an extended position in which the needle shield shields the needle of the syringe in use, and a retracted position in which the needle of the syringe is exposed; and
   a locking arrangement configured to lock said needle shield against retraction movement and which is locked and unlocked automatically during or as a result of the coupling action and reversal thereof as the housing portions are connected and disconnected, such that the needle shield is unlocked in an unlocked mode when said front and rear housing portions are connected to each other and locked in a locked mode when said housing portions are disconnected.

2. The autoinjector according to claim 1, wherein said locking arrangement comprises complementary locking surfaces (26, 28, 30) disposed on the needle shield portion (20) and the front housing portion (14), respectively.

3. The autoinjector according to claim 2, wherein said shield portion (20) is locked by a relative angular movement.

4. The autoinjector according to claim 3, wherein said complementary surfaces include an internal projection (30) on said front housing portion and a complementary groove on said shield portion, the groove having a rearward circumferential portion (26) corresponding to the locked mode and, extending therefrom, an axial portion (28) allowing relative longitudinal movement.

5. The autoinjector according to claim 4, wherein said front and rear housing portions are connected by a rotary coupling action, and said needle shield has a rearward connection interface for being engaged by a complementary forward connection interface on said rear housing portion, whereby coupling said front and rear housing portions causes said needle shield to rotate to become unlocked.

6. The autoinjector according to claim 5, wherein said forward and rearward connection interfaces comprise longitudinally engageable non-circular male (58) and female (44) plug and socket portions.

7. The autoinjector according to claim 3, wherein said front and rear housing portions are connected by a rotary coupling action, and said needle shield has a rearward connection interface for being engaged by a complementary forward connection interface on said rear housing portion, whereby coupling said front and rear housing portions causes said needle shield to rotate to become unlocked.

8. The autoinjector according to claim 7, wherein said forward and rearward connection interfaces comprise longitudinally engageable non-circular male (58) and female (44) plug and socket portions.

9. The autoinjector according to claim 1, wherein, in use, the barrel of the syringe is visible through aligned apertures (18, 32, 42) in two or more of the front housing portion, the needle shield (20), and a syringe carrier (34) when the shield is in the unlocked position, at least one of the apertures moving out of alignment when the shield is locked so the syringe is no longer visible.

10. The autoinjector according to claim 1, wherein said shield portion (20) is locked by a relative angular movement.

11. The autoinjector according to claim 10, wherein said front and rear housing portions are connected by a rotary coupling action, and said needle shield has a rearward connection interface for being engaged by a complementary forward connection interface on said rear housing portion, whereby coupling said front and rear housing portions causes said needle shield to rotate to become unlocked.

12. The autoinjector according to claim 11, wherein said forward and rearward connection interfaces comprise longitudinally engageable non-circular male (58) and female (44) plug and socket portions.

13. An autoinjector, comprising:
front (10) and rear (12) separable housing portions connectable and disconnectable by a coupling action,
the rear housing portion comprising a drive mechanism (54), and
the front housing portion being adapted in use to receive a syringe having a needle, and including an inspection window (18) through which the contents of the syringe may be viewed,
the front housing portion also including a shutter arrangement movable between an open position and a closed position, the shutter arrangement being opened when said housing portions are connected and being closed when said portions are disconnected.

14. An autoinjector, comprising:
front and rear separable housing portions configured to be reversibly coupled together,
the front housing portion being adapted in use to receive a syringe having a needle, and
the rear housing portion containing a drive mechanism that, in use, drives the syringe,
the front housing portion including a retractable needle shield movable between an extended position in which the needle shield shields the needle of the syringe, and a retracted position in which the needle of the syringe is exposed; and
a locking arrangement that, in a first mode, permits a retraction movement of the needle shield from the extended position to the retracted position and, in a second mode, locks said needle shield against retracting from the extended position to the retracted position,
said locking arrangement automatically assuming the first mode upon the front and rear housing portions being coupled together, and automatically assuming the second mode upon the front and rear housing portions being separated from each other in a decoupling action.

15. The autoinjector according to claim 14, wherein the front housing portion also includes an inspection window through which, in use, the contents of the syringe are viewable.

16. The autoinjector according to claim 15, wherein the rear housing portion comprises a bayonet coupling interface complementary to a corresponding bayonet coupling interface on the front housing portion.

17. The autoinjector according to claim 14,
wherein said front and rear housing portions are coupled to each other by way of a rotary coupling action where the front housing portion is caused to rotate relative to the rear housing portion, and
wherein said needle shield of said front housing portion is connected to a rearward connection interface that, upon said rotary coupling action for coupling the front and rear housing portions together, engages with a complementary forward connection interface on said rear housing portion and rotates said needle shield into an unlocked position free to move from the extended position to the retracted position.

18. The autoinjector according to claim 17, wherein the front housing portion also includes an inspection window through which, in use, the contents of the syringe are viewable.

19. The autoinjector according to claim 17, wherein the rear housing portion comprises a bayonet coupling interface complementary to a corresponding bayonet coupling interface on the front housing portion.

* * * * *